US008958889B2

(12) United States Patent
Walker et al.

(10) Patent No.: US 8,958,889 B2
(45) Date of Patent: Feb. 17, 2015

(54) MRI COMPATIBLE LEAD COIL

(71) Applicant: Cardiac Pacemakers, Inc., St. Paul, MN (US)

(72) Inventors: Joseph Walker, Shoreview, MN (US); G. Shantanu Reddy, Minneapolis, MN (US); Devon N. Arnholt, Shoreview, MN (US); Masoud Ameri, Maple Plain, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/015,972

(22) Filed: Aug. 30, 2013

(65) Prior Publication Data
US 2014/0067030 A1    Mar. 6, 2014

Related U.S. Application Data
(60) Provisional application No. 61/695,903, filed on Aug. 31, 2012.

(51) Int. Cl.
| A61N 1/00 | (2006.01) |
| A61N 1/05 | (2006.01) |
| A61N 1/08 | (2006.01) |

(52) U.S. Cl.
CPC ........ *A61N 1/056* (2013.01); *A61N 1/08* (2013.01); *A61N 2001/086* (2013.01)
USPC .......................................................... 607/116

(58) Field of Classification Search
CPC ....................................................... A61N 1/05
USPC .......................................................... 607/116
See application file for complete search history.

(56) References Cited

U.S. PATENT DOCUMENTS
| 3,614,692 A | 10/1971 | Rozelle et al. |
| 4,131,759 A | 12/1978 | Felkel |
(Continued)

FOREIGN PATENT DOCUMENTS
| CN | 1762510 A | 4/2006 |
| CN | 1905789 A | 1/2007 |
(Continued)

OTHER PUBLICATIONS
"High Voltage Engineering and Testing, 2nd Edition", edited by Hugh M. Ryan, Institution of Engineering and Technology, 2001, 15 pages.
(Continued)

*Primary Examiner* — Christopher D Koharski
*Assistant Examiner* — Nadia A Mahmood
(74) *Attorney, Agent, or Firm* — Faegre Baker Daniels LLP

(57) ABSTRACT

Various embodiments concern leads having low peak MRI heating for improved MRI compatibility. Various leads include a lead body having at least one lumen, a proximal end configured to interface with an implantable medical device, and a distal end. Such leads can further include a conductor extending along at least a portion of the lead body within the at least one lumen and a defibrillation coil extending along an exterior portion of the lead body and in electrical connection with the conductor, wherein at least a section of the defibrillation coil is under longitudinal compression. The longitudinal compression can lower peak MRI heating along the defibrillation coil. The longitudinal compression may maintain circumferential contact between adjacent turns of the section of the defibrillation coil.

20 Claims, 4 Drawing Sheets

(56) References Cited

U.S. PATENT DOCUMENTS

| | | |
|---|---|---|
| 4,135,518 A | 1/1979 | Dutcher |
| 4,146,036 A | 3/1979 | Dutcher et al. |
| 4,209,019 A | 6/1980 | Dutcher et al. |
| 4,253,462 A | 3/1981 | Dutcher et al. |
| 4,350,169 A | 9/1982 | Dutcher et al. |
| 4,381,013 A | 4/1983 | Dutcher |
| 4,404,125 A | 9/1983 | Abolins et al. |
| 4,437,474 A | 3/1984 | Peers-Trevarton |
| 4,484,586 A | 11/1984 | McMickle et al. |
| 4,493,329 A | 1/1985 | Crawford et al. |
| 4,574,800 A | 3/1986 | Peers-Trevarton |
| 4,643,202 A | 2/1987 | Roche |
| 4,643,203 A | 2/1987 | Labbe |
| 4,649,938 A | 3/1987 | McArthur |
| 4,869,970 A | 9/1989 | Gulla et al. |
| 5,002,067 A | 3/1991 | Berthelsen et al. |
| 5,003,975 A | 4/1991 | Hafelfinger et al. |
| 5,020,545 A | 6/1991 | Soukup |
| 5,056,516 A | 10/1991 | Spehr |
| 5,074,313 A | 12/1991 | Dahl et al. |
| 5,144,960 A | 9/1992 | Mehra et al. |
| 5,201,865 A | 4/1993 | Kuehn |
| 5,217,010 A | 6/1993 | Tsitlik et al. |
| 5,222,506 A | 6/1993 | Patrick et al. |
| 5,231,996 A | 8/1993 | Bardy et al. |
| 5,241,957 A | 9/1993 | Camps et al. |
| 5,243,911 A | 9/1993 | Dow et al. |
| 5,246,014 A | 9/1993 | Williams et al. |
| 5,259,395 A | 11/1993 | Li |
| 5,300,108 A | 4/1994 | Rebell et al. |
| 5,324,322 A | 6/1994 | Grill, Jr. et al. |
| 5,330,522 A | 7/1994 | Kreyenhagen |
| 5,354,327 A | 10/1994 | Smits |
| 5,370,666 A | 12/1994 | Lindberg et al. |
| 5,378,234 A | 1/1995 | Hammerslag et al. |
| 5,387,199 A | 2/1995 | Siman et al. |
| 5,417,208 A | 5/1995 | Winkler |
| 5,425,755 A | 6/1995 | Doan |
| 5,456,707 A | 10/1995 | Giele |
| 5,476,485 A | 12/1995 | Weinberg et al. |
| 5,483,022 A | 1/1996 | Mar |
| 5,522,872 A | 6/1996 | Hoff |
| 5,522,875 A | 6/1996 | Gates et al. |
| 5,534,018 A | 7/1996 | Wahlstrand et al. |
| 5,542,173 A | 8/1996 | Mar et al. |
| 5,545,205 A | 8/1996 | Schulte et al. |
| 5,549,646 A | 8/1996 | Katz et al. |
| 5,554,139 A | 9/1996 | Okajima |
| 5,574,249 A | 11/1996 | Lindsay |
| 5,584,873 A | 12/1996 | Shoberg et al. |
| 5,599,576 A | 2/1997 | Opolski |
| 5,609,622 A | 3/1997 | Soukup et al. |
| 5,618,208 A | 4/1997 | Crouse et al. |
| 5,727,552 A | 3/1998 | Ryan |
| 5,727,553 A | 3/1998 | Saad |
| 5,728,149 A | 3/1998 | Laske et al. |
| 5,755,742 A | 5/1998 | Schuelke et al. |
| 5,760,341 A | 6/1998 | Laske et al. |
| 5,766,227 A | 6/1998 | Nappholz et al. |
| 5,800,496 A | 9/1998 | Swoyer et al. |
| 5,810,887 A | 9/1998 | Accorti, Jr. et al. |
| 5,817,136 A | 10/1998 | Nappholz et al. |
| 5,824,026 A | 10/1998 | Diaz |
| 5,833,715 A | 11/1998 | Vachon et al. |
| 5,849,031 A | 12/1998 | Martinez et al. |
| 5,891,114 A | 4/1999 | Chien et al. |
| 5,891,179 A | 4/1999 | Er et al. |
| 5,935,159 A | 8/1999 | Cross, Jr. et al. |
| 5,957,966 A | 9/1999 | Schroeppel et al. |
| 5,957,970 A | 9/1999 | Shoberg et al. |
| 5,968,087 A | 10/1999 | Hess et al. |
| 6,016,447 A | 1/2000 | Juran et al. |
| 6,057,031 A | 5/2000 | Breme et al. |
| 6,078,840 A | 6/2000 | Stokes |
| 6,083,216 A | 7/2000 | Fischer, Sr. |
| 6,101,417 A | 8/2000 | Vogel et al. |
| 6,106,522 A | 8/2000 | Fleischman et al. |
| 6,141,593 A | 10/2000 | Patag |
| 6,143,013 A | 11/2000 | Samson et al. |
| 6,178,355 B1 | 1/2001 | Williams et al. |
| 6,192,280 B1 | 2/2001 | Sommer et al. |
| 6,208,881 B1 | 3/2001 | Champeau |
| 6,249,708 B1 | 6/2001 | Nelson et al. |
| 6,256,541 B1 | 7/2001 | Heil et al. |
| 6,259,954 B1 | 7/2001 | Conger et al. |
| 6,289,250 B1 | 9/2001 | Tsuboi et al. |
| 6,295,476 B1 | 9/2001 | Schaenzer |
| 6,304,784 B1 | 10/2001 | Allee et al. |
| 6,317,633 B1 | 11/2001 | Jorgenson et al. |
| 6,360,129 B1 | 3/2002 | Ley et al. |
| 6,400,992 B1 | 6/2002 | Borgersen et al. |
| 6,428,537 B1 | 8/2002 | Swanson et al. |
| 6,434,430 B2 | 8/2002 | Borgersen et al. |
| 6,456,888 B1 | 9/2002 | Skinner et al. |
| 6,493,591 B1 | 12/2002 | Stokes |
| 6,501,991 B1 | 12/2002 | Honeck et al. |
| 6,501,994 B1 | 12/2002 | Janke et al. |
| 6,510,345 B1 | 1/2003 | Van Bentem |
| 6,516,230 B2 | 2/2003 | Williams et al. |
| 6,526,321 B1 | 2/2003 | Spehr |
| 6,564,107 B1 | 5/2003 | Bodner et al. |
| 6,671,554 B2 | 12/2003 | Gibson et al. |
| 6,701,191 B2 | 3/2004 | Schell |
| 6,721,600 B2 | 4/2004 | Jorgenson et al. |
| 6,721,604 B1 | 4/2004 | Robinson et al. |
| 6,813,251 B1 | 11/2004 | Garney et al. |
| 6,813,521 B2 | 11/2004 | Bischoff et al. |
| 6,850,803 B1 | 2/2005 | Jimenez et al. |
| 6,854,994 B2 | 2/2005 | Stein et al. |
| 6,866,044 B2 | 3/2005 | Bardy et al. |
| 6,906,256 B1 | 6/2005 | Wang |
| 6,920,361 B2 | 7/2005 | Williams |
| 6,925,334 B1 | 8/2005 | Salys |
| 6,944,489 B2 | 9/2005 | Zeijlemaker et al. |
| 6,949,929 B2 | 9/2005 | Gray et al. |
| 6,978,185 B2 | 12/2005 | Osypka |
| 6,985,755 B2 | 1/2006 | Cadieux et al. |
| 6,985,775 B2 | 1/2006 | Reinke et al. |
| 6,993,373 B2 | 1/2006 | Vrijheid et al. |
| 6,999,818 B2 | 2/2006 | Stevenson et al. |
| 6,999,821 B2 | 2/2006 | Jenney et al. |
| 7,013,180 B2 | 3/2006 | Villaseca et al. |
| 7,013,182 B1 | 3/2006 | Krishnan |
| 7,047,075 B2 | 5/2006 | Stubbs |
| 7,047,083 B2 | 5/2006 | Gunderson et al. |
| 7,050,855 B2 | 5/2006 | Zeijlemaker et al. |
| 7,113,827 B2 | 9/2006 | Silvestri et al. |
| 7,123,013 B2 | 10/2006 | Gray |
| 7,127,294 B1 | 10/2006 | Wang et al. |
| 7,135,978 B2 | 11/2006 | Gisselberg et al. |
| 7,138,582 B2 | 11/2006 | Lessar et al. |
| 7,158,837 B2 | 1/2007 | Osypka et al. |
| 7,174,219 B2 | 2/2007 | Wahlstrand et al. |
| 7,174,220 B1 | 2/2007 | Chitre et al. |
| 7,205,768 B2 | 4/2007 | Schulz et al. |
| 7,239,916 B2 | 7/2007 | Thompson et al. |
| 7,242,987 B2 | 7/2007 | Holleman et al. |
| 7,257,449 B2 | 8/2007 | Bodner |
| 7,289,851 B2 | 10/2007 | Gunderson et al. |
| 7,363,090 B2 | 4/2008 | Halperin et al. |
| 7,369,898 B1 | 5/2008 | Kroll et al. |
| 7,378,931 B2 | 5/2008 | Odahara et al. |
| 7,388,378 B2 | 6/2008 | Gray et al. |
| 7,389,148 B1 | 6/2008 | Morgan |
| 7,453,344 B2 | 11/2008 | Maeda et al. |
| 7,535,363 B2 | 5/2009 | Gisselberg et al. |
| 7,571,010 B2 | 8/2009 | Zarembo et al. |
| 7,610,101 B2 | 10/2009 | Wedan et al. |
| 7,630,761 B2 | 12/2009 | Salo et al. |
| 7,689,291 B2 | 3/2010 | Polkinghorne et al. |
| 7,765,005 B2 | 7/2010 | Stevenson |
| 7,853,332 B2 | 12/2010 | Olsen et al. |
| 7,877,150 B2 | 1/2011 | Hoegh et al. |
| 7,912,552 B2 | 3/2011 | Przybyszewski |

(56) References Cited

U.S. PATENT DOCUMENTS

| | | |
|---|---|---|
| 7,917,213 B2 | 3/2011 | Bulkes et al. |
| 7,933,662 B2 | 4/2011 | Marshall et al. |
| 7,953,499 B2 | 5/2011 | Knapp et al. |
| 7,986,999 B2 | 7/2011 | Wedan et al. |
| 7,991,484 B1 | 8/2011 | Sengupta et al. |
| 8,000,801 B2 | 8/2011 | Stevenson et al. |
| 8,027,736 B2 | 9/2011 | Wahlstrand et al. |
| 8,032,230 B1 | 10/2011 | Cox et al. |
| 8,046,084 B2 | 10/2011 | Bodner |
| 8,099,177 B2 | 1/2012 | Dahlberg |
| 8,103,360 B2 | 1/2012 | Foster |
| 8,108,054 B2 | 1/2012 | Helland |
| 8,145,324 B1 | 3/2012 | Stevenson et al. |
| 8,170,688 B2 | 5/2012 | Wedan et al. |
| 8,200,342 B2 | 6/2012 | Stevenson et al. |
| 8,214,055 B2 | 7/2012 | Erickson |
| 8,244,346 B2 | 8/2012 | Foster et al. |
| 8,255,055 B2 | 8/2012 | Ameri |
| 8,306,630 B2 | 11/2012 | Stubbs et al. |
| 8,315,715 B2 | 11/2012 | Erickson |
| 8,332,050 B2 | 12/2012 | Perrey et al. |
| 8,335,572 B2 | 12/2012 | Ameri |
| 8,391,994 B2 | 3/2013 | Foster et al. |
| 8,401,671 B2 | 3/2013 | Wedan et al. |
| 8,543,209 B2 | 9/2013 | Tyers et al. |
| 8,543,218 B2 | 9/2013 | Erickson |
| 8,666,508 B2 | 3/2014 | Foster et al. |
| 8,666,512 B2 | 3/2014 | Walker et al. |
| 8,731,685 B2 | 5/2014 | Ameri |
| 8,744,600 B2 | 6/2014 | Perrey et al. |
| 8,798,767 B2 | 8/2014 | Foster et al. |
| 8,825,179 B2 | 9/2014 | Walker et al. |
| 8,825,181 B2 | 9/2014 | Foster et al. |
| 2002/0065544 A1 | 5/2002 | Smits |
| 2002/0072769 A1 | 6/2002 | Silvian et al. |
| 2002/0111664 A1 | 8/2002 | Bartig et al. |
| 2002/0128689 A1 | 9/2002 | Connelly et al. |
| 2002/0144720 A1 | 10/2002 | Zahorik et al. |
| 2003/0028231 A1 | 2/2003 | Partridge et al. |
| 2003/0050680 A1 | 3/2003 | Gibson et al. |
| 2003/0063946 A1 | 4/2003 | Williams et al. |
| 2003/0083723 A1 | 5/2003 | Wilkinson et al. |
| 2003/0083726 A1 | 5/2003 | Zeijlemaker et al. |
| 2003/0092303 A1 | 5/2003 | Osypka |
| 2003/0093136 A1 | 5/2003 | Osypka et al. |
| 2003/0093138 A1 | 5/2003 | Osypka et al. |
| 2003/0139794 A1 | 7/2003 | Jenney et al. |
| 2003/0140931 A1 | 7/2003 | Zeijlemaker et al. |
| 2003/0144705 A1 | 7/2003 | Funke |
| 2003/0144716 A1 | 7/2003 | Reinke et al. |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0204217 A1 | 10/2003 | Greatbatch |
| 2004/0014355 A1 | 1/2004 | Osypka et al. |
| 2004/0064161 A1 | 4/2004 | Gunderson et al. |
| 2004/0064173 A1 | 4/2004 | Hine et al. |
| 2004/0064174 A1 | 4/2004 | Belden |
| 2004/0088033 A1 | 5/2004 | Smits et al. |
| 2004/0097965 A1 | 5/2004 | Gardeski et al. |
| 2004/0122490 A1 | 6/2004 | Reinke et al. |
| 2004/0153049 A1 | 8/2004 | Hewitt et al. |
| 2004/0162600 A1 | 8/2004 | Williams |
| 2004/0167442 A1 | 8/2004 | Shireman et al. |
| 2004/0172117 A1 | 9/2004 | Hill et al. |
| 2004/0193140 A1 | 9/2004 | Griffin et al. |
| 2004/0243210 A1 | 12/2004 | Morgan et al. |
| 2004/0267107 A1 | 12/2004 | Lessar et al. |
| 2005/0030322 A1 | 2/2005 | Gardos |
| 2005/0070972 A1 | 3/2005 | Wahlstrand et al. |
| 2005/0090886 A1 | 4/2005 | MacDonald et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0136385 A1 | 6/2005 | Mann et al. |
| 2005/0177135 A1 | 8/2005 | Hildebrand et al. |
| 2005/0182471 A1 | 8/2005 | Wang |
| 2005/0197677 A1 | 9/2005 | Stevenson |
| 2005/0222642 A1 | 10/2005 | Przybyszewski et al. |
| 2005/0222656 A1 | 10/2005 | Wahlstrand et al. |
| 2005/0222657 A1 | 10/2005 | Wahlstrand et al. |
| 2005/0222658 A1* | 10/2005 | Hoegh et al. ............... 607/116 |
| 2005/0222659 A1 | 10/2005 | Olsen et al. |
| 2005/0246007 A1 | 11/2005 | Sommer et al. |
| 2005/0267556 A1 | 12/2005 | Shuros et al. |
| 2005/0272280 A1 | 12/2005 | Osypka |
| 2005/0283167 A1 | 12/2005 | Gray |
| 2006/0009819 A1 | 1/2006 | Przybyszewski |
| 2006/0030774 A1 | 2/2006 | Gray et al. |
| 2006/0037461 A1 | 2/2006 | Yasumura |
| 2006/0041293 A1 | 2/2006 | Mehdizadeh et al. |
| 2006/0041294 A1 | 2/2006 | Gray |
| 2006/0041296 A1 | 2/2006 | Bauer et al. |
| 2006/0089691 A1 | 4/2006 | Kaplan et al. |
| 2006/0089695 A1 | 4/2006 | Bolea et al. |
| 2006/0089696 A1 | 4/2006 | Olsen et al. |
| 2006/0093685 A1 | 5/2006 | Mower et al. |
| 2006/0105066 A1 | 5/2006 | Teague et al. |
| 2006/0106442 A1 | 5/2006 | Richardson et al. |
| 2006/0118758 A1 | 6/2006 | Wang et al. |
| 2006/0129043 A1 | 6/2006 | Ben-Jacob et al. |
| 2006/0167536 A1 | 7/2006 | Nygren et al. |
| 2006/0200218 A1 | 9/2006 | Wahlstrand |
| 2006/0229693 A1 | 10/2006 | Bauer et al. |
| 2006/0247747 A1 | 11/2006 | Olsen et al. |
| 2006/0247748 A1 | 11/2006 | Wahlstrand et al. |
| 2006/0252314 A1 | 11/2006 | Atalar et al. |
| 2006/0253180 A1 | 11/2006 | Zarembo et al. |
| 2006/0271138 A1 | 11/2006 | MacDonald |
| 2006/0293737 A1 | 12/2006 | Krishnan |
| 2007/0010702 A1 | 1/2007 | Wang et al. |
| 2007/0027532 A1 | 2/2007 | Wang et al. |
| 2007/0106332 A1 | 5/2007 | Denker et al. |
| 2007/0112398 A1 | 5/2007 | Stevenson et al. |
| 2007/0156205 A1 | 7/2007 | Larson et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0208383 A1 | 9/2007 | Williams |
| 2007/0255378 A1 | 11/2007 | Polkinghorne et al. |
| 2008/0009905 A1 | 1/2008 | Zeijlemaker |
| 2008/0033497 A1 | 2/2008 | Bulkes et al. |
| 2008/0039709 A1 | 2/2008 | Karmarkar |
| 2008/0049376 A1 | 2/2008 | Stevenson et al. |
| 2008/0051854 A1 | 2/2008 | Bulkes et al. |
| 2008/0057784 A1 | 3/2008 | Zarembo et al. |
| 2008/0058902 A1 | 3/2008 | Gray et al. |
| 2008/0119917 A1 | 5/2008 | Geistert |
| 2008/0125754 A1 | 5/2008 | Beer et al. |
| 2008/0129435 A1 | 6/2008 | Gray |
| 2008/0132985 A1 | 6/2008 | Wedan et al. |
| 2008/0132986 A1 | 6/2008 | Gray et al. |
| 2008/0140152 A1 | 6/2008 | Imran et al. |
| 2008/0154348 A1 | 6/2008 | Atalar et al. |
| 2008/0208290 A1 | 8/2008 | Phillips et al. |
| 2008/0243218 A1 | 10/2008 | Bottomley et al. |
| 2008/0262584 A1 | 10/2008 | Bottomley et al. |
| 2008/0269831 A1 | 10/2008 | Erickson |
| 2009/0005825 A1 | 1/2009 | MacDonald |
| 2009/0024180 A1 | 1/2009 | Kisker et al. |
| 2009/0024197 A1 | 1/2009 | Jensen |
| 2009/0099440 A1 | 4/2009 | Viohl |
| 2009/0099555 A1 | 4/2009 | Viohl et al. |
| 2009/0118610 A1 | 5/2009 | Karmarkar et al. |
| 2009/0149920 A1 | 6/2009 | Li et al. |
| 2009/0149933 A1 | 6/2009 | Ameri |
| 2009/0149934 A1 | 6/2009 | Ameri et al. |
| 2009/0198314 A1 | 8/2009 | Foster et al. |
| 2009/0204171 A1 | 8/2009 | Ameri |
| 2009/0210022 A1 | 8/2009 | Powers |
| 2009/0270948 A1 | 10/2009 | Nghiem et al. |
| 2009/0270956 A1 | 10/2009 | Vase et al. |
| 2009/0281608 A1 | 11/2009 | Foster |

(56) References Cited

U.S. PATENT DOCUMENTS

| | | |
|---|---|---|
| 2010/0010602 A1 | 1/2010 | Wedan et al. |
| 2010/0016935 A1 | 1/2010 | Strandberg et al. |
| 2010/0103215 A1 | 4/2010 | Iriguchi |
| 2010/0106215 A1 | 4/2010 | Stubbs et al. |
| 2010/0114277 A1 | 5/2010 | Zhao et al. |
| 2010/0125320 A1 | 5/2010 | Polkinghorne et al. |
| 2010/0137928 A1 | 6/2010 | Duncan et al. |
| 2010/0174348 A1 | 7/2010 | Bulkes et al. |
| 2010/0174349 A1 | 7/2010 | Stevenson et al. |
| 2010/0234929 A1 | 9/2010 | Scheuermann |
| 2010/0249892 A1 | 9/2010 | Bulkes et al. |
| 2010/0292744 A1 | 11/2010 | Hill et al. |
| 2010/0331936 A1 | 12/2010 | Perrey et al. |
| 2011/0060394 A1 | 3/2011 | Poore |
| 2011/0079423 A1 | 4/2011 | Zhao et al. |
| 2011/0087299 A1 | 4/2011 | Ameri |
| 2011/0087302 A1 | 4/2011 | Ameri |
| 2011/0093054 A1 | 4/2011 | Ameri et al. |
| 2011/0160805 A1 | 6/2011 | Erbstoeszer et al. |
| 2011/0160816 A1 | 6/2011 | Stubbs et al. |
| 2011/0160817 A1 | 6/2011 | Foster et al. |
| 2011/0160818 A1 | 6/2011 | Struve |
| 2011/0160828 A1 | 6/2011 | Foster et al. |
| 2011/0160829 A1 | 6/2011 | Foster et al. |
| 2011/0208280 A1 | 8/2011 | Li et al. |
| 2011/0218422 A1 | 9/2011 | Atalar et al. |
| 2011/0238146 A1 | 9/2011 | Wedan et al. |
| 2011/0288403 A1 | 11/2011 | Kondabatni et al. |
| 2012/0016451 A1 | 1/2012 | Struve et al. |
| 2012/0022356 A1 | 1/2012 | Olsen et al. |
| 2012/0035698 A1 | 2/2012 | Johnson et al. |
| 2012/0053662 A1 | 3/2012 | Foster et al. |
| 2012/0109270 A1 | 5/2012 | Foster |
| 2012/0143273 A1 | 6/2012 | Stubbs et al. |
| 2012/0161901 A1 | 6/2012 | Stevenson et al. |
| 2012/0179233 A1 | 7/2012 | Wedan et al. |
| 2012/0253340 A1 | 10/2012 | Stevenson et al. |
| 2012/0271394 A1 | 10/2012 | Foster et al. |
| 2013/0116764 A1 | 5/2013 | Walker et al. |
| 2013/0158641 A1 | 6/2013 | Foster et al. |
| 2013/0190849 A1 | 7/2013 | Perrey et al. |
| 2013/0190850 A1 | 7/2013 | Wedan et al. |
| 2013/0282093 A1 | 10/2013 | Walker et al. |
| 2013/0325093 A1 | 12/2013 | Foster |
| 2014/0114383 A1 | 4/2014 | Foster et al. |
| 2014/0155972 A1 | 6/2014 | Foster et al. |
| 2014/0324139 A1 | 10/2014 | Foster et al. |

FOREIGN PATENT DOCUMENTS

| | | |
|---|---|---|
| CN | 101039619 A | 9/2007 |
| EP | 0897997 B1 | 2/2003 |
| EP | 1594564 A1 | 11/2005 |
| EP | 1852810 B1 | 11/2007 |
| JP | 2004141679 A | 5/2004 |
| JP | 2005501673 A | 1/2005 |
| JP | 2005515852 A | 6/2005 |
| JP | 2005515854 A | 6/2005 |
| WO | WO9606655 A1 | 3/1996 |
| WO | WO03063953 A2 | 8/2003 |
| WO | WO03089045 A2 | 10/2003 |
| WO | WO2004073791 A1 | 9/2004 |
| WO | WO03063946 A2 | 4/2005 |
| WO | WO2005030322 A1 | 4/2005 |
| WO | WO2006105066 A2 | 3/2006 |
| WO | WO2006093685 A1 | 9/2006 |
| WO | WO2007047966 A2 | 4/2007 |
| WO | WO2007089986 A1 | 8/2007 |
| WO | WO2007118194 A2 | 10/2007 |
| WO | WO2008051122 A1 | 5/2008 |
| WO | WO2009137186 A1 | 11/2009 |
| WO | WO2010078552 A1 | 7/2010 |

OTHER PUBLICATIONS

Avalanche Breakdown, Wikipedia Article, captured Apr. 6, 2010, [http://en.wikipedia.org/wiki/Avalanche_breakdown].
Basso, Christophe, "SPICE Model Simulates Spark-Gap Arrestor", Electronics Design, Strategy, and News (EDN), Jul. 3, 1997, 4 pages.
Citel Inc., Data Sheet, BH Series 2 Electrode Miniature Gas Discharge Tube Surge Arrester—8mm, May 14, 2009, 2 pages.
Gray, Robert W. et al., "Simple design changes to wires to substantially reduce MRI-induced heating at 1.5 T: implications for implanted leads", Magnetic Resonance Imaging 23 (2005) 887-891.
Hayes, David L., Chapter 4, "Generator and Lead Selection" from book entitled "Cardiac Pacing and Defibrillation a Clinical Approach", John Wiley & Sons, (c) 2000 Mayo Foundation, p. 129-157.
International Search Report and Written Opinion issued in PCT/US2008/085518 on Oct. 29, 2009, 15 pages.
International Search Report and Written Opinion issued in PCT/US2009/032838, mailed May 4, 2009, 14 pages.
International Search Report and Written Opinion issued in PCT/US2009/038629, mailed Jun. 29, 2009, 11 pages.
International Search Report and Written Opinion issued in PCT/US2009/056843, mailed Dec. 29, 2009, 13 pages.
International Search Report and Written Opinion issued in PCT/US2010/024062, mailed Sep. 27, 2010.
International Search Report and Written Opinion issued in PCT/US2010/033686 on Aug. 10, 2010, 12 pages.
International Search Report and Written Opinion issued in PCT/US2010/048620, mailed Apr. 5, 2011, 10 pages.
International Search Report and Written Opinion issued in PCT/US2010/053223, mailed Dec. 27, 2010, 11 pages.
International Search Report and Written Opinion issued in PCT/US2010/055130, mailed Mar. 10, 2011, 11 pages.
International Search Report and Written Opinion issued in PCT/US2010/055653, mailed Feb. 1, 2011, 14 pages.
International Search Report and Written Opinion issued in PCT/US2011/052541, dated Mar. 9, 2012, 22 pages.
International Search Report and Written Opinion issued in PCT/US2012/055673, mailed Dec. 13, 2012, 10 pages.
International Search Report and Written Opinion issued in PCT/US2013/057732, mailed Dec. 13, 2013, 11 pages.
Invitation to Pay Additional Fees and Partial Search Report, dated Aug. 17, 2009, issued in PCT/US2008/085533, 6 pages.
Invitation to Pay Additional Fees and Partial Search Report, issued in PCT/US2010/024062, mailed May 7, 2010.
Partial International Search Report issued in PCT/US2011/052541, mailed Dec. 6, 2011, 4 pages.
Partial International Search Report issued in PCT/US2013/013432, mailed Jul. 17, 2013, 6 pages.
Partial International Search Report issued in PCT/US2013/037432, mailed Jul. 17, 2013, 6 pages.
Static Spark Gap Analysis, captured Dec. 24, 2002, [http://www.richieburnett.co.uk/static.html].
International Search Report and Written Opinion issued in PCT/US2013/065517, mailed Dec. 20, 2013, 11 pgs.
File History for U.S. Appl. No. 11/015,807, filed Dec. 17, 2004 to Cooke, Daniel J. et al.
International Search Report and Written Opinion issued in PCT/US2013/037432, mailed Nov. 19, 2013, 17 pages.
Third Party Submission Under 37 CFR 1.290 filed in U.S. Appl. No. 14/056,746 on May 20, 2014, 13 pages.

* cited by examiner

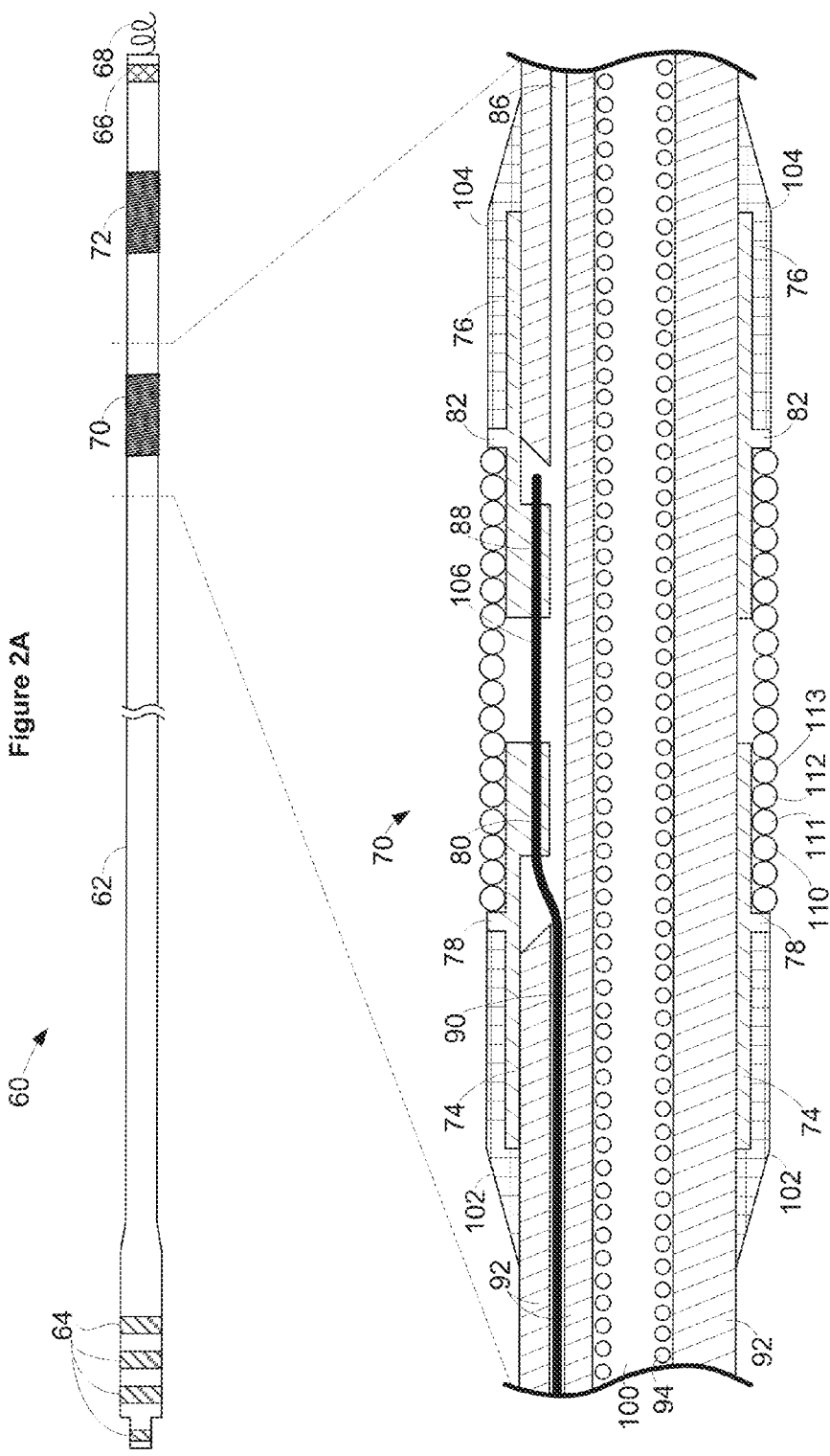

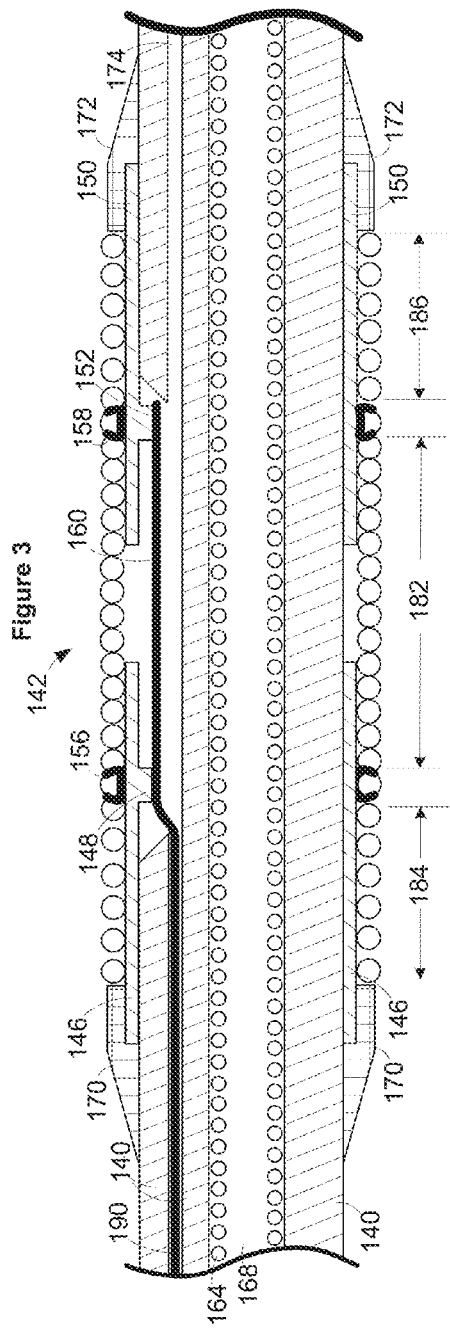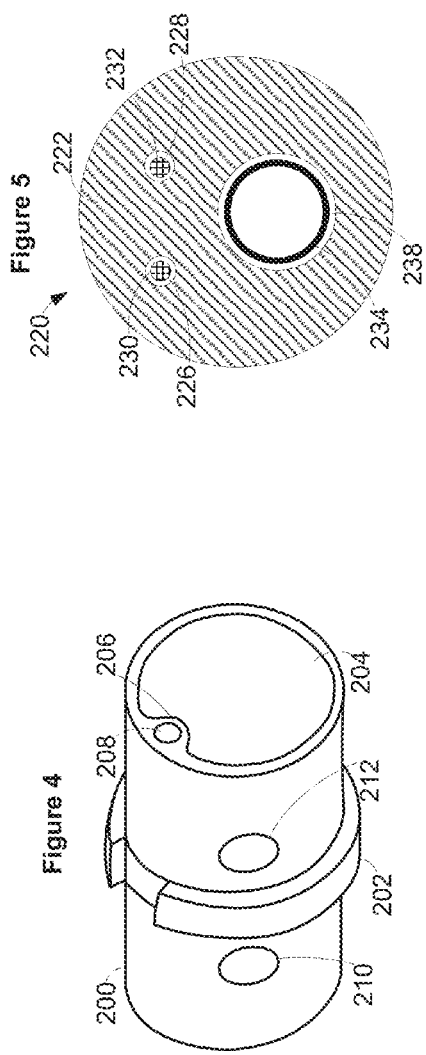

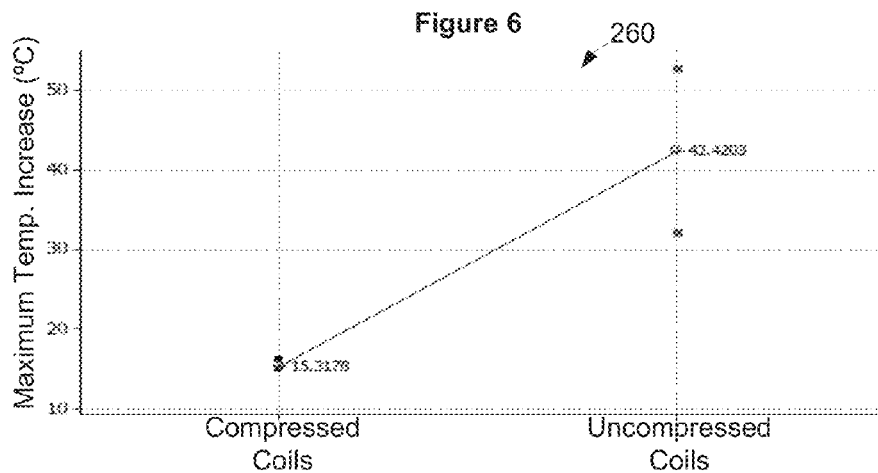
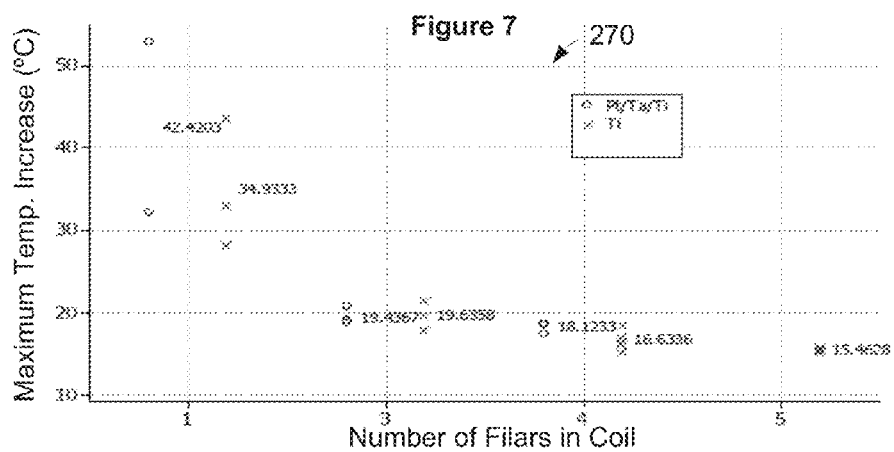
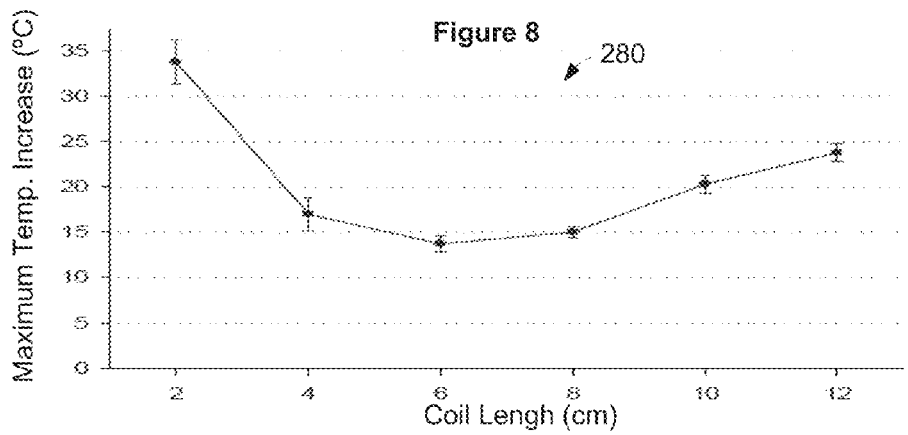

MRI COMPATIBLE LEAD COIL

CROSS-REFERENCE TO RELATED APPLICATION

This application claims priority to U.S. Provisional Application No. 61/695,903, filed Aug. 31, 2012, which is herein incorporated by reference in its entirety.

TECHNICAL FIELD

The present disclosure relates to implantable medical devices. More particularly, the present disclosure relates to MRI-compatible tachycardia lead constructions.

BACKGROUND

Magnetic resonance imaging (MRI) is a non-invasive imaging procedure that utilizes nuclear magnetic resonance techniques to render images of anatomy within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to a conducting element in contact with the tissue, which may lead to elevated temperatures at the point of contact. The degree of tissue heating is typically related to factors such as the length of the lead, the conductivity or impedance of the lead, and the surface area of the lead electrodes. Exposure to a magnetic field may also induce an undesired voltage on the lead.

SUMMARY

Example 1 concerns a lead having low peak MRI heating, the lead comprising: a lead body having at least one lumen, a proximal end configured to interface with an implantable medical device, and a distal end; a cable conductor extending along at least a portion of the lead body within the at least one lumen; a coil extending along a portion of the distal end of the lead body, at least a section of coil exposed along the portion of the lead body and configured to deliver electrical stimulation therapy, the section of the coil under longitudinal compression to lower peak MRI heating along the section of the coil; and at least two couplings mechanically and electrically connecting the cable conductor to the coil, where the at least two couplings maintain longitudinal compression of the section of the coil.

In example 2, an embodiment of example 1, wherein the section of the coil is between the at least two couplings.

In example 3, an embodiment of either example 1 or 2, wherein the cable conductor is in tension between the at least two couplings, the tension in the cable conductor maintaining the longitudinal compression within the coil.

In example 4, an embodiment of any of examples 1-3, wherein the longitudinal compression forces each turn of the section of the coil to maintain circumferential contact with adjacent turns of the section of the coil.

In example 5, an embodiment of any of examples 1-4, wherein the coil comprises a second section that is either proximal or distal of the section of the coil, the second section not under longitudinal compression.

In example 6, an embodiment of any of examples 1-5, wherein the at least two couplings comprise at least two rings, the cable conductor extends within each of the rings, and each of the rings is at least partially within a lumen of the coil.

In example 7, an embodiment of any of examples 1-6, wherein each of the at least two couplings are crimped to the cable conductor and welded to the coil.

In example 8, an embodiment of any of examples 1-7, wherein the outer surface of the coil is formed from a non-oxidizing metal.

In example 9, an embodiment of any of examples 1-8, wherein the outer surface of the coil is formed from platinum.

In example 10, an embodiment of any of examples 1-9 further comprising a second coil positioned distally along the lead body with respect to the coil, wherein the second coil is not under longitudinal compression.

Example 11 concerns a lead having low peak MRI heating, the lead comprising: a lead body having at least one lumen, a proximal end configured to interface with an implantable medical device, and a distal end; a cable conductor extending along at least a portion of the lead body within the at least one lumen; a coil extending along a portion of the distal end of the lead body, at least a section of the coil exposed along the portion of the lead body and configured to deliver electrical stimulation therapy; a proximal coupling mechanically and electrically connecting the cable conductor to the coil; and a distal coupling mechanically and electrically connecting the cable conductor to the coil distally with respect to the proximal coupling to maintain the proximal coupling and the distal coupling in a spaced apart relationship that lowers peak MRI heating along the coil.

In example 12, an embodiment of example 11, wherein the section of the coil is between the proximal coupling and the distal coupling in the spaced apart relationship and is under longitudinal compression.

In example 13, an embodiment of any of examples 1-12, wherein the longitudinal compression maintains circumferential contact between adjacent turns of the section of the coil.

In example 14, an embodiment of any of examples 1-13, wherein the longitudinal compression in the section of the coil is maintained at least in part by tension within the cable conductor.

In example 15, an embodiment of any of examples 1-14, wherein the length of the coil is between about 4 and about 8 centimeters.

In example 16, an embodiment of any of examples 1-13, wherein the coil comprises at least three filars.

Example 17 concerns a lead having low peak MRI heating, the lead comprising a lead body having at least one lumen, a proximal end configured to interface with an implantable medical device, and a distal end; a conductor extending along at least a portion of the lead body within the at least one lumen; and a coil electrode extending along a portion of the distal end of the lead body and in electrical connection with the conductor, at least a section of the coil electrode under longitudinal compression.

In example 18, an embodiment of example 17, wherein the longitudinal compression lowers peak MRI heating along the coil electrode.

In example 19, an embodiment of either of examples 17 or 18, wherein the longitudinal compression maintains circumferential contact between adjacent turns of the section of the coil electrode.

In example 20, an embodiment of any of examples 17-19, further comprising a proximal coupling mechanically connected to the conductor and the coil; and a distal coupling mechanically connected to the conductor and the coil electrode positioned distal with respect to the proximal coupling.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A is a schematic view of a lead having two defibrillation coils.

FIG. 2B is a cross-sectional view of a distal portion of the lead of FIG. 2A having the proximal defibrillation coil.

FIG. 3 is a cross-sectional view of a distal portion of a lead having a defibrillation coil.

FIG. 4 is a schematic view of a coupling that can mechanically and electrically connect a defibrillation coil and a cable conductor.

FIG. 5 is a cross-sectional view a lead body.

FIG. 6 is plot of data comparing heating along compressed and uncompressed coils in a simulated MRI environment.

FIG. 7 is a plot of data comparing heating along coils having different numbers of filars in a simulated MRI environment.

FIG. 8 is a plot of data comparing heating along coils of different lengths in a simulated MRI environment.

Figure 1:
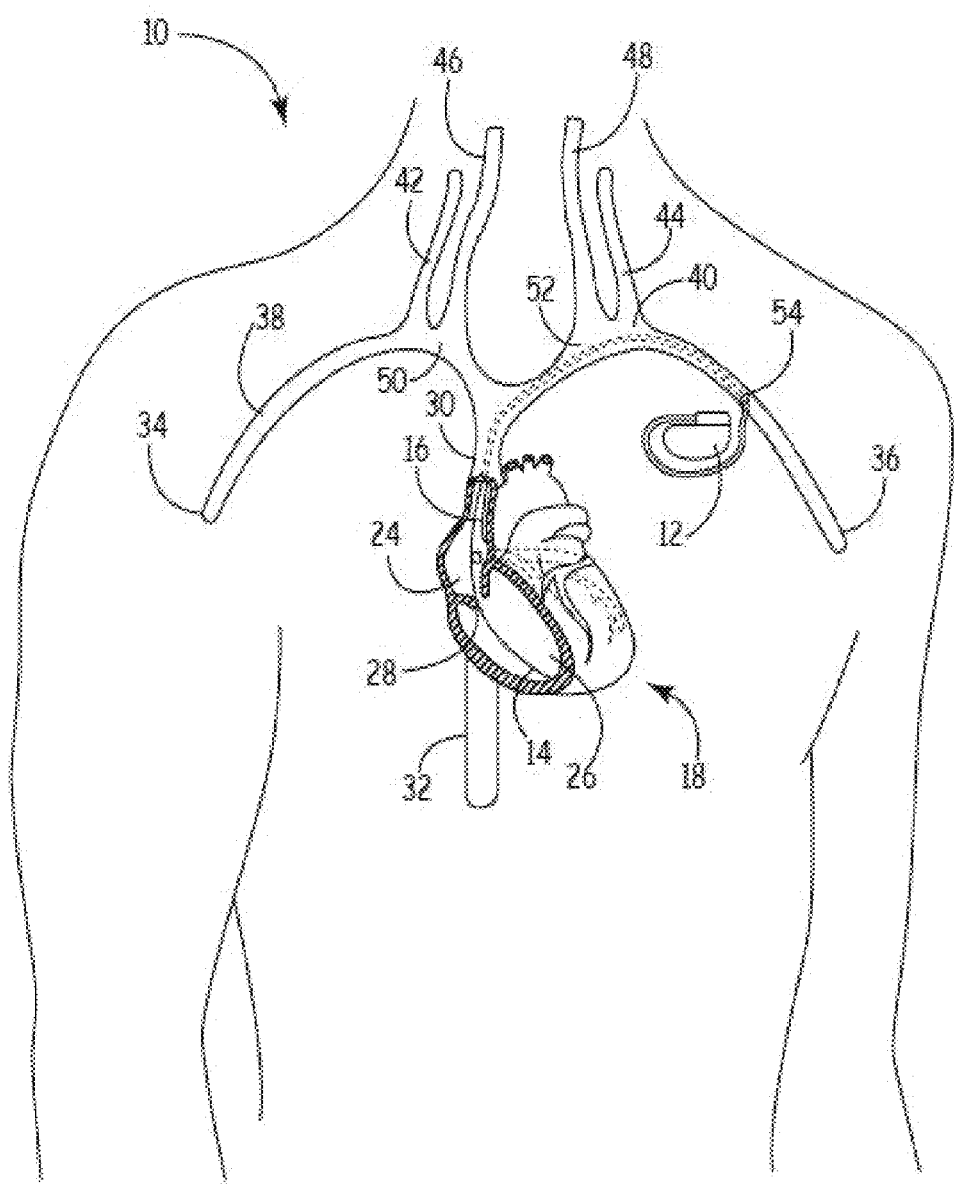
FIG. 1 is a schematic view of a cardiac rhythm management (CRM) system including a pulse generator and leads implanted in a patient's heart.

While the subject matter of the present disclosure is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Magnetic resonance imaging is a useful tool for non-invasively visualizing and analyzing the internal anatomy of patients. However, the radio frequency (RF) fields generated in an MRI environment can induce currents in conductive elements, such as a conductor of a medical electrical lead of an implantable pulse generator or other medical device. Currents may be induced by RF fields in an elongated conductor (e.g., a cable) along an insulated section of the lead and then conducted to a non-insulated element (e.g., a stimulating coil or electrode) of the lead that contacts the patient's tissue. The inducted MRI energy may then convert to heat energy when dissipating to the patient's tissue. If high enough in temperature, the heating caused by the dissipating energy may be harmful to the tissue that is adjacent to the lead. Minimizing the peak heating associated with inducted RF energy may allow a lead to be safely used in an MRI environment. This disclosure concerns, among other things, lead features that minimize peak heating associated with inducted RF energy.

FIG. 1 is a schematic view of a cardiac rhythm management (CRM) system 10 according to various embodiments of the present disclosure. As shown in FIG. 1, the CRM system 10 includes a pulse generator 12 coupled to a plurality of leads 14, 16 deployed in a patient's heart 18. As further shown in FIG. 1, the heart 18 includes a right atrium 24 and a right ventricle 26 separated by a tricuspid valve 28. During normal operation of the heart 18, deoxygenated blood is fed into the right atrium 24 through the superior vena cava 30 and the inferior vena cava 32. The major veins supplying blood to the superior vena cava 30 include the right and left axillary veins 34 and 36, which flow into the right and left subclavian veins 38 and 40. The right and left external jugular 42 and 44, along with the right and left internal jugular 46 and 48, join the right and left subclavian veins 38 and 40 to form the right and left brachiocephalic veins 50 and 52, which in turn combine to flow into the superior vena cava 30.

The leads 14, 16 operate to convey sensed bioelectrical signals and electrical stimulation between the heart 18 and the pulse generator 12. In the illustrated embodiment, lead 14 is implanted in the right ventricle 26, and lead 16 is implanted in the right atrium 24. In other embodiments, the CRM system 10 may include additional or alternative leads, e.g., a lead extending into a coronary vein for stimulating the left ventricle in a bi-ventricular pacing or cardiac resynchronization therapy system. In some embodiments, one or more leads may not be in contact with the heart and may sense and/or deliver stimulation to the heart remotely (e.g., implanted in a subcutaneous, non-intrathoracic location). In some other embodiments, one or more leads of the present disclosure are implanted to stimulate an organ other than the heart. As shown, the leads 14, 16 enter the vascular system through a vascular entry site 54 formed in the wall of the left subclavian vein 40, extend through the left brachiocephalic vein 52 and the superior vena cava 30, and are implanted in the right ventricle 26 and right atrium 24, respectively. In some other embodiments, the leads 14, 16 may enter the vascular system through the right subclavian vein 38, the left axillary vein 36, the left external jugular 44, the left internal jugular 48, or the left brachiocephalic vein 52.

The pulse generator 12 is typically implanted subcutaneously within an implantation location or pocket in the patient's chest or abdomen. The pulse generator 12 may be an implantable medical device known in the art or later developed, such as for delivering an electrical therapeutic stimulus to the patient. In various embodiments, the pulse generator 12 is a pacemaker, an implantable cardiac defibrillator, and/or includes both pacing and defibrillation capabilities. The portion of the leads 14, 16 extending from the pulse generator 12 to the vascular entry site 54 are also located subcutaneously or submuscularly. The leads 14, 16 are each connected to the pulse generator 12 via proximal connectors. Any excess lead length, i.e., length beyond that needed to reach from the pulse generator 12 location to the desired intracardiac implantation site, is generally coiled up in the subcutaneous pocket near the pulse generator 12.

FIG. 2A illustrates a cross-sectional view of a lead 60. The lead 60 can, for example, correspond to any of the leads 14, 16 of FIG. 1 or any other lead referenced herein. The lead 60 includes a plurality of proximal contacts 64 on the proximal end of the lead 60. The proximal end of the lead is sized and shaped to be inserted into a header or other interface for making electrical connections between the proximal contacts 64 and different channels of a pulse generator. The proximal contacts 64 can be connected to conductors which extend within one or more lumens in the lead body 62 to electrically connect with respective electrical elements on the distal end of the lead. Such elements can include proximal coil 70, distal coil 72, electrode 66, and conductive fixation element 68. A pulse generator or other implantable medical device can independently sense and/or deliver stimulation through the electrical elements of the lead 60 by respective conductors within the lead body 62.

Electrode 66 and/or conductive fixation element 68 can be used for sensing electrical signals and/or delivering electrical energy (e.g., pacing pulses) to the heart. Each of electrode 66 and fixation element 68 can be connected to respective electrical conductors (e.g., cable conductor, coil conductors) that extend within one or more lumens within the lead body 62 to make respective electrical connections with the proximal contacts 64. While electrode 66 is illustrated as one ring electrode in FIG. 2A, a different configuration and/or number of electrodes could be provided (e.g., one or more ring electrodes can be provided, such as two ring electrodes). In some embodiments, the electrode 66 includes platinum or titanium coated with a combination of iridium oxide (IrOx), titanium/nickel (Ti/Ni), black platinum (Pt black), or tantalum oxide (TaO). The configuration of the conductive fixation element 68 in FIG. 2A is a helix, however various other embodiments could additionally or alternatively include tines or other fixation elements. It is noted that some embodiments many not include the electrode 66 and/or the conductive fixation element 68.

Either or both of the proximal and distal coils 70 and 72 may be used to deliver a high voltage defibrillation therapy signal to the heart. The lead 60 can be arranged in the heart (e.g., in the manner of FIG. 1) such that the defibrillation signal delivered through the coil 70 depolarizes a critical mass of the heart muscle to terminate an arrhythmia and allow a normal sinus rhythm to be reestablished. The coils 70 and 72 are exposed on the exterior of the lead 60 to facilitate the stimulation of tissue. For example, a portion or the entirety of the proximal coil 70 is not covered by insulation and is able to directly contact tissue adjacent the coil 70. The coils 70 and 72 surround respective longitudinal portions of the lead body 62, with the longitudinal portions of the lead body 62 being within the respective lumens of the coils 70 and 72. Each of the coils 70 and 72 can be connected to respective electrical conductors (e.g., cable conductor, coil conductors) that extend within one or more lumens within the lead body 62 to make respective electrical connections with the proximal contacts 64. While two coils 70 and 72 are illustrated in FIG. 2A, various embodiments of the lead 60 may include only one coil, such as the proximal coil 70, or a greater number of coils, such as three or four coils.

FIG. 2B is a cross-sectional view of the lead 60 focusing on the proximal coil 70. The cross-sectional view shows that the lead body 62 comprises a plurality of lumens, including a cable lumen 86 and a coil lumen 100, formed within the lead body material 92. The lead body material 92 can be a polymer such as urethane or silicone. The lead body material 92 can be extruded to form a round exterior shape and a plurality of internal lumens (e.g., as shown in FIG. 5). A coil conductor 94 is contained within the coil lumen 100. The coil conductor 94 can electrically connect with the electrode 66 and/or the conductive fixation element 68. In some embodiments the coil conductor 94 is a unifilar cathode coil that connects with one of the distal electrical elements of the lead 60 (e.g., the electrode 66 or the conductive fixation element 68). It is noted that a unifilar coil conductor 94 can help minimize heating associated with an MRI procedure at an electrically connected electrode 66. An insulator (not illustrated) can be placed within the lumen of the coil conductor 94 to insulate the coil conductor 94 from a stylet, guidewire, sensor, or other member placed within the coil lumen 100, however the absence of a separate insulator can maximize the space for passage of a stylet or other member within the lumen of the coil conductor 94.

As shown in FIG. 2B, the coil 70 comprises a plurality of turns (e.g., turns 110-113) of one or more filars. While a single filar is used within the coil 70 in some embodiments, two, three, four, five, or more filars can be used to form the coil 70. In some embodiments, a defibrillation coil, such as coil 70, is made from three or more filars to minimize peak heating along the defibrillation coil associated with an MRI procedure. As will be further demonstrated herein, the degree of peak heating along a coil is variable based on the number of filars. Reduction in peak heating is correlated with an increasing number of filars. In particular, there is a large drop in peak heating between a coil with two filars and a coil with three filars, where the three filar coil is associated with less peak heating. As such, in various embodiments, the coil 70 comprises three or more filars.

The proximal coil 70 is held between a proximal coupling 74 and a distal coupling 76. The proximal coupling 74 can be a ring placed over the lead body 62. An example coupling is shown in FIG. 4 and is further described herein. The distal coupling 76 can be identical to the proximal coupling 74, the distal coupling 76 being oriented in the opposite direction on the lead body 62 (i.e. placed over the lead body 62 in the opposite orientation as the proximal coupling 74 such that the couplings face each other). A proximal taper feature 102 can be molded or adhered over a portion of the proximal coupling 74. Likewise, a distal taper feature 104 can be molded or adhered over a portion of the distal coupling 76. The proximal and distal taper features 102 and 104 can secure the couplings 74 and 76 to the lead body 62 and/or electrically insulate the couplings 74 and 76. In some cases, a taper feature can fix a coupling to a lead body. In some cases, the proximal taper feature 102 is at least in part proximal of the proximal coupling 74 and blocks the proximal coupling 74 from moving proximally in response to a proximally directed force placed on the proximal coupling 74 (e.g., by the coil 70 as will be further explained herein). In some cases, the distal taper feature 104 is at least in part distal of the distal coupling 76 and blocks the distal coupling 76 from moving distally in response to a distally directed force placed on the distal coupling 76 (e.g., by the coil 70). The proximal and distal taper features 102 and 104 can be formed by polymer and/or medical adhesive. In some cases, the proximal and distal taper features 102 and 104 can be molded over the couplings 74 and 76 and the lead body 62.

As shown in FIG. 2B, a void in the lead body material 92 has been formed by removing a portion of the lead body material 92 (e.g., cut away in a skive process), the void providing access to the cable lumen 86. The removed portion of the lead body material 92 may be shorter than the length of the coil 70. The cable conductor 90 can be run through the cable lumen 86 (e.g., from the proximal end) and bent to extend out of the cable lumen 86 to the area from which the portion of the lead body material 92 was removed. The proximal coupling 74 can include a connector 80. The connector 80 can mechanically and electrically connect to the cable conductor 90. In some embodiments, the connector 80 is crimped around the cable conductor 90. In some embodiments, the connector 80 is welded to the cable conductor 90. Other types of mechanical and electrical connections can be made between a coupling and a cable conductor. Distal coupling 76 can include a connector 88 which can further connect to the cable conductor 90 in ways described herein (e.g., by crimping the connector 88 over the cable conductor 90). As shown in FIG. 2B, the same cable conductor 90 is directly connected to each of the proximal and distal couplings 74 and 76 at respective proximal and distal locations along the cable conductor 90 by crimping. A space is provided between the distal end of the proximal coupling 74 and the proximal end of the distal coupling 76. A section 106 of the cable conductor 90 spans the space between the distal end of the proximal coupling 74 and the proximal end of the distal coupling 76. While two couplings are provided in the embodiment of FIG. 2B for the coil 70, a different number of couplings can be provided in various others for a particular coil. For example, a coil may be electrically and mechanically connected to a single coupling at multiple locations along the lengths of coupling and the coil (e.g., one proximal connection and one distal connection).

The proximal coupling 74 includes a stop 78 that can be in direct contact with the most proximal turn of the coil 70. Likewise, the distal coupling 76 includes a stop 82 that can be in contact with the most distal turn of the proximal coil 70. Each of the stops 78 and 82 can comprise a projection that extends outward from a circumferential surface of the proximal coupling 74 or the distal coupling 76. In some embodiments, the stops 78 and 82 are posts. In some other embodiments, the stops 78 and 82 are ridges. In various embodiments, the coil 70 will hug the lead body 62 and the circumferential surfaces of the proximal coupling 74 and the distal coupling 76 when the coil 70 is over the lead body 60 and the couplings 74 and 76. In these cases, the coil 70 will exert a downward force on the lead body 60 and the circumferential surfaces of the proximal coupling 74 and the distal coupling 76.

The coil 70 can be subject to longitudinal compression between the stops 78 and 82 (longitudinal in this sense of being along the length of the particular section of the lead). In various embodiments, the coil 70 is biased to spread out over a particular length to an uncompressed state. A state of longitudinal compression can be created and maintained within the coil 70 by forcing the length of the coil 70 to be less than the biased uncompressed length. For example, the coil 70 may be biased to intrinsically spread out to a length greater than the distance between stops 78 and 82, but the coil 70 is compressed when fit between the stops 78 and 82. The proximal stop 78 (or other feature) of the proximal coupling 74 can exert a distally directed force on the most proximal turn of the coil 70 while the distal stop 82 (or other feature) of the distal coupling 76 can exert a proximally directed force on the most distal turn of the coil 70, thereby compressing the coil 70 between the stops 78 and 82. In some embodiments, the coil may be compressed to a particular degree. For example, the compression in a coil can be between about 1 and 15 Newton (N). In some embodiments, the compression in a coil is between about 5 and 15 (N). Other ranges and measures of coil compression can be used in various configurations. The compression can be measured based on the force the coil 70 applies to a feature with which it is engaged, such as stop 78. A coil can be configured to apply a reactive force when compressed based on the type of material forming the coil, the thickness of the coil, and the spring constant of the coil, among other factors.

The longitudinal compressive force can be supported by various features. In some cases, the couplings 74 and 76 can be mechanically supported by the lead body material In some cases, the connectors 80 and 88 of the couplings 74 and 76 can be connected to respective proximal and distal sections along the cable conductor In these cases, the coil 70 compresses longitudinally and the longitudinal compression is supported by the section 106 of the cable conductor 90 which is then placed in tension. In this way, tension within the cable conductor 90 can maintain the longitudinal compression of the coil 70. Additionally or alternatively, the couplings 74 and 76 can be braced by the proximal and distal taper features 102 and 104, which can transfer proximal and distal forces, respectively, to the lead body material 92 to mechanically support the longitudinal compression of the coil 70.

The longitudinal compressive force can force each turn of the coil 70 to directly contact a proximally adjacent turn and a distally adjacent turn around the circumference of the lead body 62 with no space between the adjacent coil filars. For example, the proximal side of turn 111 is in direct contact with the distal side of turn 110 and the distal side of turn 111 is in direct contact with the proximal side of turn 112. This relationship can exist for a plurality of the turns along the coil 70 (e.g., all of the turns of a coil except for the most proximal turn and the most distal turn). In various embodiments, the contact between the sides of the turns can be circumferential about the lead body 62, such that the sides of adjacent turns are in direct contact entirely around the lead body 62 for each turn. The longitudinal compression may keep adjacent turns in direct contact with each other around the circumference of the lead body 62 despite bending of the lead, wherein the bending might otherwise change the dimension of the lead and cause some turns to separate. Longitudinal compression can inhibit fluids from seeping between adjacent turns and/or from tissue wedging between the adjacent turns.

The longitudinal compressive force can provide various advantages for lowering peak temperature increases associated with MRI procedures. The longitudinal compression can force adjacent turns of the defibrillation coil together around the circumference of the lead body to allow inducted MRI energy to directly conduct between turns and not require conduction solely around each turn of the defibrillation coil (i.e. the energy can short circuit between turns). Where multiple filars are used, inducted MRI energy is able to directly conduct between different filars that are adjacent instead of only conducting around each turn through each filar. These aspects allow the RF energy to spread out along the turns of the coil and be less concentrated as the energy dissipates to tissue and converts to heat energy. If the energy was not able to directly conduct between the turns then the energy would be concentrated in fewer turns and filars, causing the RF energy to escape to tissue in higher concentrations along smaller areas of the coil, leading to higher temperature spikes. As such, a longitudinally compressed coil can make use of more of the defibrillation coil to shed RF energy and avoid concentrated MRI heating.

It is noted that while the embodiment of FIGS. 2A-B illustrates two coils 70 and 72, a greater or lesser number of coils can be provided in various other embodiments. In some embodiments, multiple coils along a lead body can be under longitudinal compression. In some cases, the proximal coil 70 is subject to longitudinal compression while the distal coil 72 is not subject to longitudinal compression. Such a configuration may be particularly suited to applications where MRI heating is experienced to a much greater degree in a proximal coil than a distal coil and the lead must be more flexible along the distal coil than the proximal coil because the distal coil is intended to be introduced into a more dynamic heart environment than the proximal coil.

FIG. 3 illustrates a cross sectional view of an area of a lead body having a coil 142. The coil 142 can be used to deliver energy as referenced herein. The coil 142 could be a part of a lead, such as a lead of FIGS. 1 and 2A. The cross-sectional view of FIG. 3 shows that the lead body comprises a plurality of lumens, including cable lumen 174 and coil lumen 168 formed within the lead body material 140. A coil conductor 164 is contained within the coil lumen 168 which can electrically connect with one or more electrodes (e.g., electrode 66 of FIG. 2A).

The coil 142 is disposed over a first coupling 146 and a second coupling 150. The first coupling 146 can be a ring placed over the lead body. The second coupling 150 can be identical to the first coupling 146 but is oriented in the opposite direction, as discussed herein. The first coupling 146 can be proximal of the second coupling 150. A first taper feature 170 can be molded or adhered over a portion of the first coupling 146 and a second taper feature 172 can be molded or adhered over a portion of the second coupling 150. The taper sections 170 and 172 can secure the couplings 146 and 150 to the lead body and/or electrically insulate the couplings 146 and 150. A void in the lead body material 140 can be formed by removing a portion of the lead body material 140, providing access to the cable lumen 174. The cable conductor 190 can be run through the cable lumen 174 and bent to extend out of the cable lumen 174 to the area from which the portion of the lead body material 140 was removed.

The embodiment of FIG. 3 can have the same configuration of the embodiment of FIG. 2B except for the couplings 146 and 150 are of a different configuration and the coil 142 has multiple sections in the embodiment of FIG. 3. However, embodiments within the scope of this disclosure can be modified with the features of other embodiments, including the embodiments of FIGS. 2B and 3. While crimping was described to make mechanical and electrical connections between the couplers and cable conductor in the embodiment of FIG. 2B, welding is described in the embodiment of FIG. 3. Each of the coupling 146 and 150 can be rings with a respective connector 148 and 152 which can be welded to the cable conductor 190. In some configurations, the connector 148 of the first coupling 146 can have a hole from an exterior of the connector 148 to an inner surface or lumen of the coupling 146. Likewise, the connector 152 of the second coupling 150 can have a hole from an exterior of the connector 152 to an inner surface or lumen of the second coupling 150. The holes can be used to weld (e.g., laser weld) the cable conductor 190 to the insides of the couplings 146 and 150 along the connectors 148 and 152. In some embodiments, the connectors 148 and 152 can have separate lumens in which the cable conductor 190 can be inserted to facilitate a weld or other type of connection (e.g., a crimp).

The coil 142 is mechanically and electrically connected to the couplings 146 and 150 by welding, as shown by welds 156 and 158. Welds 156 and 158 can fix particular portions of the coil 142 to the couplings 146 and 150. For example, a particular turn of the coil 142 can be welded to coupling 146 and another turn can be welded to coupling 150. By fixing particular portions of the coil 142, various different sections of the coil 142 can be defined. The proximal section 184 of the coil 142 is proximal of the proximal mechanical connection (e.g., the weld 156 between the coil 142 and the coupling 146) and distal of the first taper feature 170. The proximal section 184 is uncompressed and as illustrated the turns are separated such that the sides of adjacent turns are not in contact with each other. Being uncompressed, the proximal section 184 of the coil 142 is able to assume its bias length. The middle section 182 of the coil 142 is the middle section of the coil 142 between the mechanical connections (i.e. the welds 156 and 158) between the coil 142 and the couplings 146 and 150. The middle section 182 of the coil is compressed because the bias length (e.g., the length the section of coil would stretch if in an uncompressed state) of the middle section 182 is greater than the distance between the mechanical attachments between the coil 142 and the couplings 146 and 150. The distal section 186 is distal of the distal mechanical connection (i.e. the weld 158 between the coil 142 and the second coupling 150) and proximal of the second taper feature 172. The distal section 186 is uncompressed and as illustrated the turns are separated such that the sides of adjacent turns are not in contact with each other. The distal section 186 of the coil 142 is able to assume its bias length. It is noted that in various embodiments, multiple sections of a coil can be compressed to different degrees (e.g., greater or less compressive force in each section and/or greater or less deviations from the bias length of the particular sections).

A section 160 of the cable conductor 190 can mechanically support the longitudinal compression in the middle section 182 of the coil 142. The section 160 of the cable conductor 190 is defined between the mechanical connections of the cable conductor 190 to the couplings 146 and 150. The section 160 of the cable conductor 190 is in tension because the middle section 182 of the coil 142 is under compression and applies proximal and distal forces on the first coupling 146 and the second coupling 150 respectively. In this way, the cable conductor 190 can maintain the longitudinal compression in the coil.

As discussed herein, the longitudinal compression within the coil 142 can facilitate the dispersion of inducted MRI energy from an MRI procedure and minimize peak heating. The embodiment of FIG. 3, where some sections of the coil 142 are uncompressed while at least one section is compressed, can direct the RF energy as desired. Specifically, more of the RF energy is likely to disperse along the compressed middle section 182 than the outer proximal and distal uncompressed sections 184 and 186. Different configurations of compressed and uncompressed coil sections can be formed, depending on where mechanical connections are made to fix various areas or turns of the coil to the lead body. In this way, the dispersal of inducted MRI energy along a coil can be directed to one or more sections of the coil, the heating along the coil thereby also being controlled based on the directed dispersal of RF energy.

In some embodiments, a compressed coil may not necessarily have contact between the sides of each adjacent coil. The MRI heating may be lowered in such embodiments even though the sides of adjacent coil turns are not in contact with one another. Even without circumferential contact between the sides of adjacent turns of a compressed coil, the coil may still experience less peak heating in a MRI environment compared to an uncompressed coil. A compressed coil will have closer spaced turns, and therefore more dense turns per unit length, as compared to a similar but uncompressed coil. The greater density of turns per unit length provides greater surface area to dissipate inducted MRI energy into the tissue. Accordingly, a coil may be under compression to space the turns closer together to lower peak MRI heating. However, significantly less peak heating is expected from coils compressed such that the sides of each turn of the coil contacts the adjacent turns of the coil because such a configuration allows the inducted RF energy to quickly dissipate in a less concentrated manner by directly conducting between the turns instead of solely around each turn.

FIG. 4 illustrates a coupling 200 that can be used in various embodiments. The coupling 200 shown in FIG. 4 is a ring, however other shapes can alternatively be used. The coupling 200 can be made from various materials, including a conductive metal such as titanium, MP35N, or platinum, among others. The coupling 200 can be fabricated by an electrical discharge machining process. The coupling 200 can fit over a lead body (e.g., a polymer tube having one or more lumens) by the lead body being inserted into the lumen 204 of the coupling 200 and the coupling 200 being run over the lead body to a predetermined position (e.g., immediately proximal or distal of a coil also over the lead body). The coupling 200 can make mechanical connections with conductors, such as cable conductors and coil conductors. The coupling 200 includes a connector 206 which has a lumen 208 sized to accept a cable conductor. The connector 206 is configured to deform under pressure in a crimping operation to pinch around the cable conductor within the lumen 208 to mechanically and electrically connect the cable conductor to the coupling 200. In some cases, the connector 206 can be shaped for welding to the cable connector, such as by having a hole from the exterior surface to the lumen 204 that can facilitate welding a conductor to the inside surface of the lumen 204. The coupling 200 includes a stop 202 which can be a projection from the circumferential surface of the coupling 200. The stop feature 202 can engage a coil to compress the coil (e.g., the stops can exert a compressive force on each of a proximal end and a distal end of a coil and the coil can exert an equal force on each of the stops). The coupling 200 can include one or more holes 210 and 212 which can be used to mechanically secure the coupling 200 to a lead body. For example, if a molding or reflow process is used to secure the coupling 200 to a lead body, melted polymer or adhesive can flow into the holes 210 and 212 to mechanically bind the coupling 200 to other components of the lead, such as the lead body material. The application of medical adhesive can also cause the adhesive to flow into one or both of the holes 202 and 212. Such a molding or reflow process, or the application of medical adhesive, can further form the proximal taper feature 102 and the distal taper feature 104 of FIG. 2B to secure the coupling 200 to a lead body. In the embodiments referenced herein, a coil can be welded to a coupling. For example, one or more turns of a coil can be welded to a stop 202 and/or a circumferential surface of the coupling 200 (e.g., as in FIG. 3). In some embodiments, a weld can span the circumference of the coupling and the coil (e.g., following a turn of the coil around the lead body). In some other embodiments, welding between a coupling and a coil is performed in one or more discrete spots.

While the couplings illustrated herein for mechanically and electrically connecting the cable conductor to the defibrillation coil are rings, other configurations are contemplated herein. For example, the couplings may not be rings, but may nevertheless provide for electrical and/or mechanical connections to each of the cable conductor and the defibrillation coil. In some cases, a coupling may have two ends with two connectors, each of the connectors configured to mechanically and electrically connect to one or both of the cable conductor and the defibrillation coil (e.g., by crimping and/or welding). Moreover, while multiple separate electrical and mechanical connections are shown and described between a cable conductor and a coil via multiple couplings, not all embodiments are so limited. For example, a coil with a compressed section may have a single electrical and mechanical connection with a conductor extending within the lead.

FIG. 5 shows a cross sectional view of a lead body 220. The view could be of the lead body of FIG. 2. The lead body 220 is formed by lead body material 222, which can be, for example, urethane, silicone, or another polymer. One or more lumens can be formed in the lead body material 222, such as cable conductor lumens 226 and 228, which can respectively contain cable conductors 230 and 232. The cable conductors 230 and 232 can electrically connect with respective defibrillation coils as discussed herein. The cable conductors 230 and 232 may be braided strands of MP35N alloy with a silver core, for example. Coil lumen 238 can also be formed within the lead body material 222. One or more coil conductors can be placed within one or more lumens of the lead body 220. For example, coil conductor 234 is within the coil lumen 238. As shown in FIG. 5, two or more of the conductive cables 230 and 232 and the coil conductor 234 can extend in parallel through the lead in separate lumens to electrically connect with respective distal elements (e.g., a coil, an electrode).

FIG. 6 shows a plot 260 of data collected in a series of tests evaluating peak increases in heating along defibrillation coils in a simulated MRI environment. For the tests, a group of platinum clad defibrillation coils were compressed and then subject to a simulated MRI field. Another group of platinum clad defibrillation coils were subject to the simulated MRI field but were uncompressed. Temperature measurements were made along the coils as they were subjected to the simulated MRI field. As shown in plot 260, the peak heating increase along the compressed coils was 27 degrees Celsius less than the peak heating increase along the uncompressed defibrillation coils. Lower peak heating indicates that the compressed coils would be less likely to heat adjacent tissue to an unacceptable level. Accordingly, the compression of coils can help a lead safely handle RF energy inducted during a MRI procedure.

It is noted that the drop in peak heating along a compressed coil is less for some metals forming the exterior of a coil as compared to some other metals forming the exterior of a coil. For example, the drop in peak heating along a compressed coil having an MP35N exterior surface is less as compared to a compressed coil having a platinum exterior surface. For some metals, compression might not decrease peak heating along the coil. Coils having exteriors formed from a noble metal, such as platinum, experience significantly greater drops in peak heating when compressed. In some cases, it is the type of metal that forms the exterior surface of the coil, and not necessarily the type of metal forming the interior of the coil, that affects the degree to which heating can be minimized by coil compression. It is thought that the formation of insulating layers (e.g., an oxide layer) on the exterior surface of some of the metals, such as some titanium alloys, inhibits conduction of inducted MRI energy between the turns of the coils, while such an insulating layer does not form on non-oxidizing metals. In some lead embodiments with decreased peak heating, a first material forms an interior of a coil and a second metal forms an exterior surface of the coil. The second metal may be a coating on the first metal. In some embodiments, the exterior surface of a coil is formed by a non-oxidizing metal. In some embodiments, the exterior surface of a coil is formed by a noble metal. In some embodiments, the exterior surface of a coil is formed by platinum. In some embodiments, the interior of a coil is formed by an oxidizing metal. In some embodiments, the interior of a coil is formed by MP35N.

FIG. 7 shows a plot 270 of data collected in a series of tests evaluating the increase in heating along defibrillation coils in a simulated MRI environment. For the tests, defibrillation coils having different numbers of coil filars were subject to a simulated MRI field. Each defibrillation coil was connected to a cable conductor. It is noted that the cable conductor is the component that typically receives the RF energy in an MRI environment, the energy then being conducted to a defibrillation coil for dispersion. Temperature measurements were made along the coils as they were subject to the simulated MRI field. As shown in the plot 270, the maximum temperature increase due to MRI heating decreases with an increasing number of filars. In particular, a large drop in maximum temperature increase due to MRI heating was recorded between one and three filars, a difference of approximately 15 degrees Celsius. A coil in accordance with the present disclosure can have any number of filars. However, in some embodiments, a coil can have three or more filars to minimize peak heating associated with a MRI environment. In some embodiments, a coil having three filars may be preferred because the plot 270 shows only a minimal decrease in peak heating beyond three filars and a greater number of filars can add complexity to the lead and/or impact the mechanical properties of the lead. However, in some embodiments, a coil can have four or five filars. Any lead of the present disclosure may have a coil composed of any number of filars as described above.

FIG. 8 shows a plot 280 of data collected in a series of tests evaluating the increase in heating along defibrillation coils in a simulated MRI environment. For the tests, defibrillation coils having different lengths were subject to a simulated MRI field. Temperature measurements were made along the coils as they were subject to the simulated MRI field. As shown in the plot 280, the maximum temperature increase due to the MRI heating decreased within a range of coil lengths. As indicated by plot 280, coils having lengths between about 4 and about 8 centimeters (cm) may experience less peak heating while coils shorter than about 4 cm may experience greater peak heating and coils longer than about 8 cm may also experience greater peak heating. As indicated by plot 280, coils having lengths between 5 and 7 cm may experience less peak heating while coils shorter than 5 cm may experience greater peak heating and coils longer than 7 cm may also experience greater peak heating. Accordingly, in embodiments of the present disclosure a coil may have a length between 4 and 8 cm, and more specifically between 5 and 7 cm. In some embodiments, a coil having a length of approximately 6 cm may experience less peak heating than longer or shorter coils. In some embodiments, a coil having a length of approximately 6 cm may experience the least MRI heating.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A lead having low peak MRI heating, the lead comprising:
    a lead body having at least one lumen, a proximal end configured to interface with an implantable medical device, and a distal end;
    a cable conductor extending along at least a portion of the lead body within the at least one lumen;
    a coil extending along a portion of the distal end of the lead body, at least a section of coil exposed along the portion of the lead body and configured to deliver electrical stimulation therapy, the section of the coil under longitudinal compression to lower peak MRI heating along the section of the coil; and
    at least two couplings mechanically and electrically connecting the cable conductor to the coil, where the at least two couplings maintain longitudinal compression of the section of the coil.

2. The lead of claim 1, wherein the section of the coil is between the at least two couplings.

3. The lead of claim 1, wherein the cable conductor is in tension between the at least two couplings, the tension in the cable conductor maintaining the longitudinal compression within the coil.

4. The lead of claim 1, wherein the longitudinal compression forces each turn of the section of the coil to maintain circumferential contact with adjacent turns of the section of the coil.

5. The lead of claim 1, wherein the coil comprises a second section that is either proximal or distal of the section of the coil, the second section not under longitudinal compression.

6. The lead of claim 1, wherein the at least two couplings comprise at least two rings, the cable conductor extends within each of the rings, and each of the rings is at least partially within a lumen of the coil.

7. The lead of claim 1, wherein each of the at least two couplings are crimped to the cable conductor and welded to the coil.

8. The lead of claim 1, wherein the outer surface of the coil is formed from a non-oxidizing metal.

9. The lead of claim 1, wherein the outer surface of the coil is formed from platinum.

10. The lead of claim 1, further comprising a second coil positioned distally along the lead body with respect to the coil, wherein the second coil is not under longitudinal compression.

11. A lead having low peak MRI heating, the lead comprising:
    a lead body having at least one lumen, a proximal end configured to interface with an implantable medical device, and a distal end;
    a cable conductor extending along at least a portion of the lead body within the at least one lumen;
    a coil extending along a portion of the distal end of the lead body, at least a section of the coil exposed along the portion of the lead body and configured to deliver electrical stimulation therapy;
    a proximal coupling mechanically and electrically connecting the cable conductor to the coil; and
    a distal coupling mechanically and electrically connecting the cable conductor to the coil distally with respect to the proximal coupling to maintain the proximal coupling and the distal coupling in a spaced apart relationship that lowers peak MRI heating along the coil.

12. The lead of claim 11, wherein the section of the coil is between the proximal coupling and the distal coupling in the spaced apart relationship and is under longitudinal compression.

13. The lead of claim 12, wherein the longitudinal compression maintains circumferential contact between adjacent turns of the section of the coil.

14. The lead of claim 12, wherein the longitudinal compression in the section of the coil is maintained at least in part by tension within the cable conductor.

15. The lead of claim 11, wherein the length of the coil is between about 4 and about 8 centimeters.

16. The lead of claim 11, wherein the coil comprises at least three filars.

17. A lead having low peak MRI heating, the lead comprising:
    a lead body having at least one lumen, a proximal end configured to interface with an implantable medical device, and a distal end;
    a conductor extending along at least a portion of the lead body within the at least one lumen; and a coil electrode extending along a portion of the distal end of the lead body and in electrical connection with the conductor, at least a section of the coil electrode under longitudinal compression.

18. The lead of claim 17, wherein the longitudinal compression lowers peak MRI heating along the coil.

19. The lead of claim 18, wherein the longitudinal compression maintains circumferential contact between adjacent turns of the section of the coil electrode.

20. The lead of claim 17, further comprising:
a proximal coupling mechanically connected to the conductor and the coil electrode; and
a distal coupling mechanically connected to the conductor and the coil electrode positioned distal with respect to the proximal coupling.

* * * * *